(12) United States Patent
Biber

(10) Patent No.: US 12,704,567 B2
(45) Date of Patent: Aug. 11, 2026

(54) METHOD FOR OPERATING AN IMAGING MODALITY OF A MAGNETIC RESONANCE SYSTEM, AND MAGNETIC RESONANCE SYSTEM

(71) Applicant: Siemens Healthineers AG, Forchheim (DE)

(72) Inventor: Stephan Biber, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 127 days.

(21) Appl. No.: 18/609,481

(22) Filed: Mar. 19, 2024

(65) Prior Publication Data

US 2024/0319299 A1 Sep. 26, 2024

(30) Foreign Application Priority Data

Mar. 20, 2023 (DE) ..................... 10 2023 202 427.6

(51) Int. Cl.
*G01R 33/36* (2006.01)
*A61B 5/055* (2006.01)
*G01R 33/54* (2006.01)
*G01R 33/565* (2006.01)

(52) U.S. Cl.
CPC .............. *G01R 33/36* (2013.01); *A61B 5/055* (2013.01); *G01R 33/543* (2013.01); *G01R 33/56509* (2013.01)

(58) Field of Classification Search
CPC .................. G01R 33/36; G01R 33/543; G01R 33/56509; G01R 33/283; G01R 33/48; A61B 5/055
See application file for complete search history.

(56) References Cited

U.S. PATENT DOCUMENTS

2013/0127467 A1* 5/2013 Yokoi .................... G01R 33/34 324/318
2014/0073904 A1 3/2014 Biber

FOREIGN PATENT DOCUMENTS

DE 102012214148 A1 2/2014
DE 102012216327 B4 1/2021

OTHER PUBLICATIONS

English translation of DE102012214148A1 provided by Espacenet. 2025 (Year: 2025).*
Froidevaux, Romain et al., High-resolution short-T2 MRI using a high-performance gradient, Magn Reson Med. 2020, vol. 84(4), pp. 1933-1946; https://onlinelibrary.wiley.com/doi/epdf/10.1002/mrm.28254.

* cited by examiner

*Primary Examiner* — Rishi R Patel
(74) *Attorney, Agent, or Firm* — Lempia Summerfield Katz LLC

(57) ABSTRACT

A method for operating an imaging modality of a magnetic resonance system and magnetic resonance system. At least one item of environmental information in an environment of the imaging modality is detected with at least one detection unit (of the magnetic resonance system. A potential start time is defined depending on the at least one detected item of environmental information. At least one component of the imaging modality is activated depending on the potential start time.

14 Claims, 3 Drawing Sheets

1
2
3
4
5
6
7
8
9
10
11
17
Z
Y 16,29
31
16,29
13
24
23
16,22
16,29
16,31
16,19
7
16,31
16,19
1
16'
11
16,31
12

28
20
30
32
9
36
14
15
15
15
15

T
18
T3
33
35
21
T2
T4
27
25
T1
34
26

METHOD FOR OPERATING AN IMAGING MODALITY OF A MAGNETIC RESONANCE SYSTEM, AND MAGNETIC RESONANCE SYSTEM

CROSS REFERENCE TO RELATED APPLICATIONS

This application claims the benefit of DE 10 2023 202 427.6 filed on Mar. 20, 2023, which is hereby incorporated by reference in its entirety.

FIELD

Embodiments relate to a method for operating an imaging modality of a magnetic resonance system.

BACKGROUND

In nuclear spin tomography strong radio-frequency fields are used to excite the spins in the body of a patient. Fields in the range of up to 40 μT at frequencies of up to 300 MHz or more are generated by pulse amplifiers with transmit powers of several 10 kW.

High-end systems in MRT (magnetic resonance tomography) are equipped with ever stronger gradient fields, that are intended to make new (research) applications possible. Such applications lie above all in the area of diffusion-weighted imaging. In Froidevaux et al., High-resolution short-T2 MRI using a high-performance gradient. Magn Reson Med., advantages of the PETRA or ZTE sequence with gradient strengths of 200 mT/m are shown, that show marked improvements compared to weaker gradient strengths and also other sequences for imaging of materials with a short T2*. This is based on the fact that the readout time with extremely strong gradients is advantageously short and thus the T2* decay during the readout process may be kept short. Thus, higher resolutions and the acquisition of materials with even shorter T2* becomes possible.

For example, the high-end systems mentioned above have the need for high energy in MRT. With the need for high energy or high energy consumption, as well as the high costs for a user of such a device, this is associated with a high CO2 emission, if for example the energy were to be obtained from fossil fuels. The energy consumption is determined by various components. For example, a system of MR system in "Off mode" consumes energy for cooling the magnet. In a "Ready-to-Scan mode" and a "Scanning mode" the system likewise needs energy. In today's systems a few or many subsystems are not switched after an examination of a patient from a "Scan mode" into the "Ready-to-Scan mode" because it would take too long to start them up again. The problem that often arises here is that information as to when the next scan may be started is not available early enough. The possible energy saving that would be produced by shutting down these further components is not realized nowadays because information is not available or cannot be used that prewarns the system to start up specific subsystems before that next scan.

BRIEF SUMMARY AND DESCRIPTION

The scope of the present disclosure is defined solely by the claims and is not affected to any degree by the statements within this summary. The present embodiments may obviate one or more of the drawbacks or limitations in the related art. Independent of the grammatical term usage, individuals with male, female or other gender identities are included within the term.

Embodiments provide a reduction in an energy consumption or an energy requirement of a magnetic resonance system.

Embodiments provide a method for operating an imaging modality of a magnetic resonance system, wherein at least one item of environmental information in an environment of the imaging modality is detected with at least one detection unit of the magnetic resonance system, depending on the at least one detected item of environmental information a potential start time is defined and depending on the potential start time at least one component of the imaging modality is activated.

The method provides a magnetic resonance system and for example a corresponding imaging modality of the magnetic resonance system to be operated more efficiently. By the method the energy consumption of the magnetic resonance system and for example of the imaging modality may for example be reduced.

Specifically an improvement or an increase in efficiency of the "Ready-to-Scan mode" of the magnetic resonance system may be carried out with the method. Such a "Ready-to-Scan mode" is to be understood as the magnetic resonance system being able, after a predetermined or specific time, to begin or to carry out a scan or a measurement process on a patient. In this predetermined or specific time for example subsystems or components of the magnetic resonance system that are still switched off or shut down will be switched on in order to be able to be used for the scan mode or measurement process.

For example the at least one component is to be understood as a part system or a subsystem of the magnetic resonance system, such as for example a modulator for creation of radio-frequency fields or gradient fields. For example the at least one component may involve units, systems, hardware components and/or software components of the magnetic resonance system and/or of the imaging modality. For example the at least one component is needed for carrying out a measurement process or scan process on a patient by the imaging modality.

The advantage produced by the activation of the at least one component for example is that, unlike today's systems, a respective component of the imaging modality or of the magnetic resonance system may be controlled or prepared or preconditioned or activated adapted individually to the respective situation. This is of advantage compared to today's systems, since with today's systems part systems are switched off or shut down, that is put into a "Sleep mode", as soon as for example an examination table or patient table "PTAB" in is in a "Home position" or basic position or if no scan has been requested for 10 minutes for example. The component in this case is started up again at the start of the scan, that leads to an increased energy consumption. This is improved with the help of the method.

The magnetic resonance system may have the at least one detection unit or a number of detection units. The at least one detection unit or a number of detection units may make use of a very wide variety of detection principles. The at least one detection unit may be configured and arranged in such a way that the environment of the imaging modality may be detected or supervised at least in some areas, preferably completely.

The at least one detected item of environmental information or a number, for example various, items of environmental information may be provided or transferred to a control apparatus or to a control and processing system of the magnetic resonance system for example, so that the potential start time may be established and thus defined.

The potential start time may involve a point in time as from which the imaging modality may carry out a measurement process or scan process of a patient. Likewise the start time may involve a time at which the wide diversity of components and/or systems of the imaging modality must be started up or activated.

For example the start time involves a point in time as from which the imaging modality is in the “Ready-to-Scan mode”.

Furthermore, for example at least one corresponding activation signal or control signal may be generated on the basis of the potential start time, in order to transfer said signal to the at least one component.

The method may involve a computer-implemented method.

In an embodiment, the start time may be defined on the basis of a detection time of the detection of the at least one item of environmental information. The point in time at which the at least one item of environmental information is detected may be used for the definition or establishment of the start time. The detection time may be used for example as reference value or as relation for the determination of the start time. The at least one detected item of environmental information may for example involve an event or a state relating to the magnetic resonance system, so that the detection time may be used as the point in time for this event, in order, on the basis of this event, to determine the subsequent steps or points in time for activation of the at least one component and/or the number of components of the imaging modality.

Specifically, it may be determined on the basis of the detection time and a duration how long it is still likely to take for a measurement process of a patient to be carried out with the imaging modality. Starting from the detection time, furthermore various steps, such as preparation steps, measurement steps and/or evaluation steps, of the imaging modality may be predicted or forecast. Thus, for example the execution sequence of measurement processes of the magnetic resonance system may be organized more efficiently.

In an embodiment, on the basis of the detection times and the at least one item of environmental information, a point in time may be predicted as potential start time at which a measurement process on a patient may be begun with the imaging modality. With the predicted or forecast point in time the imaging system and for example the components of the imaging system may be activated or operated in a more energy-saving and particular more efficient manner. Depending on this forecast or predicted point in time, the at least one component and/or number of components or systems of the imaging modality may be prepared for the existing or future measurement process. Here the at least one component and/or the number of components may be preconfigured, preconditioned and/or adapted accordingly. This makes it possible to save energy since, depending on this forecast point in time, the at least one component and/or number of components will only be moved or switched from an idle mode into an operating mode when the measurement process is due immediately.

For example components of the imaging modality, that have a time-intensive start-up process or restart process, are switched on or started up first in respect of the predicted start time. Components that have a shorter start-up process or take a shorter time to switch back on may just be switched on just a short time before the measurement process. This makes it possible for components to be activated in good time or for components only to be shut down unnecessarily at all or be put into an idle mode depending on whether the measurement process is due immediately or still lies far further in the future from the detection time.

Thus, based on the predicted point in time in respect of the measurement process, taking into account a reduction of the energy consumption, the imaging modality is activated or put into an operating mode accordingly.

In an embodiment, on the basis of the potential start time, at the least one component of the imaging modality may be activated in such a way that an activation time of the at least one component and/or an operating mode of the at least one component is defined. By the potential start time the at least one component may be preconfigured or preconditioned in respect of a potential measurement process of the imaging modality to be carried out, so that the at least one component may be prepared in an energy-saving manner for the potential measurement process. On the basis of the potential start time and for example of the point in time at which a measurement process may be carried out on a patient, it may be defined at what point in time the at least one component is to be activated or at what point in time the at least one component is to be switched from an idle mode to an active mode for example.

It may be defined or determined with the help of the activation time, as from which point in time the at least one component must be active in order for a measurement process to be able to be carried out on the patient by the imaging modality. Furthermore a current and/or future functional state or state of the at least one component, for example in respect of a measurement process to be carried out on a patient, may be defined with the operating mode.

In an embodiment, depending on the potential start time, further components of the imaging modality may be activated. On the basis of the potential start time and the at least one item of environmental information, an order of the components of the imaging modality to be activated is defined. For example, starting from the potential start time, such as for example the point in time of a possible beginning of a measurement process, a number of components, such as part systems of the imaging modality, are activated accordingly. Thus an order of the components to be activated may be determined or defined in order on the one hand to be able to prepare the imaging modality for a measurement process to be carried out and to activate the components in the specific or particular order in such a way that an energy consumption of the imaging modality is kept low.

Depending on the potential start time, it may be determined or defined at what point in time a respective component of the imaging modality should have been activated.

In an embodiment a respective activation time may be defined by the order for each component. In order to be able to operate the imaging modality with a lower or low energy consumption it is advantageous when the components or imaging modality are controlled or activated individually. Depending on when a potential measurement process is carried out with the imaging modality and/or how long the time remaining takes until potential measurement process will be carried out, the components may be activated individually. Accordingly there is an adapted activation and for example an adapted activation order of individual or of all components of the imaging modality. In this case it may be noted how long a respective component needs to be put or to be switched into an active state with respect to the potential start time.

Thus the order involves a specific order so that the individual components of the imaging modality are able to be activated and thus are able to be prepared for a potential measurement process with the imaging modality.

In an embodiment, depending on the at least one activated component of the imaging modality, an optical, acoustic and/or haptic notification may be output to a patient and/or to an operator of the imaging modality. By the respective activated component for example the current system state or operating state of the imaging modality may be characterized, so that with the respective activated component a respective system state of the imaging modality may be output visually, acoustically and/or haptically to the patient and/or to the operator.

For example a corresponding electronic output unit may be provided to enable the notification to be output accordingly.

In an embodiment, a position of a patient in relation to the imaging modality may be detected as the first item of environmental information with a first detection unit. The potential start time is additionally defined depending on the first item of environmental information.

In an embodiment, the potential start time may additionally be defined as a function of a past measurement process of the imaging modality. For example measurement processes of the imaging modality carried out may be stored as datasets and stored for example in a database of the magnetic resonance system. In the past measuring processes or in the measuring processes carried out in the past, points in time and/or time intervals and/or periods of time relating to the past measurement process are provided. With the aid of these the potential start time for activating the at least one component may be determined or defined for the current case concerned.

For example, in the past measurement process or in a number of past measurement processes, information or data may be stored for when specific components have been controlled or activated with respect to a measurement process carried out in the past. Account may thus be taken for example of when a corresponding component was activated for a measurement process carried out in the past in relation to detected information or to a respective situation. In its turn this may be used to define the potential start time and thus to activate the at least one component and/or the number of components more efficiently in order to be able to reduce the energy consumption of the magnetic resonance system.

In an embodiment, a position of a patient in relation to the imaging modality may be detected with a first detection unit as the first item of environmental information. The potential start time is additionally defined as a function of the first item of environmental information.

For example the magnetic resonance system, as well as the at least one detection unit, may have further detection units similar to the first detection unit. For example the first detection unit may be an element of a detection system of the magnetic resonance system. In order better to be able to define the potential start time and for example to be able to define it more accurately, it is advantageous for a number of items of environmental information, for example various items of environmental information to be taken into account.

For example the first detection unit may involve a camera or a camera system, with which the position of the patient in relation to the imaging modality may be detected. The respective position may be determined or calculated by image processing. For example the first item of environmental information may thus be checked, or it may be established whether the patient is located on an examination table or a patient table of the imaging modality. Should the patient already be located on the examination table or be lying on it, then it may be considered on the system side that there is to be a measurement process of the patient immediately. This may be taken into account for the determination or definition of the potential start time.

Furthermore the first detection unit may be a weight sensor, a pressure sensor and/or a proximity sensor. As a result, the position, for example the current position of the patient, may likewise be detected or established here.

In an embodiment movements of a patient and/or of an operator in the environment of the imaging modality may be detected as the second item of environmental information. The potential start time is additionally determined as a function of the second item of environmental information.

For example the second detection unit may be an element of the measurement system, i.e. of a higher-ranking measurement system of the magnetic resonance system. For example the detection unit may be configured as a movement sensor or camera system, in order accordingly to detect movements or sequences of movements in the environment of the imaging modality. In this case for example a distinction may be made by image processing or an image processing program as to whether the detected movement involves the movement of the patient the movement of an operator, i.e. a medical technician for example. Should for example a movement of the operator in the direction away from the imaging modality be detected or established as the movement, it may be deduced from this that the operator is leaving an examination room relating to the magnetic resonance system and thus that an immediate measurement process of the patient will be undertaken.

The second item of environmental information may thus involve a variant of the at least one item of environmental information. Thus various items of environmental information may be taken into account in the definition of the potential start time.

In an embodiment, with a third detection unit, an opening and/or a closing of a door of the examination room in which the imaging modality is arranged may be defined as the third item of environmental information. The potential start time is additionally defined as a function of the diameter environmental information.

The third detection unit may for example include a unit or an element of the higher-ranking detection system of the magnetic resonance system.

For example the third detection unit, like the first and/or second detection unit, may include a single-part detection unit or a multi-part detection unit.

The imaging modality may be arranged in the examination room, i.e. in a room in which an examination of a patient may be carried out by the imaging modality. To this end the examination room may have at least one door or a number of doors as entries and exits. These doors or the door may be detected or supervised with the help of the third detection unit. One or a number of electrical or electronic door contacts or door contact sensors may be involved here. Thus it may be detected when a patient enters the examination room and when a patient leaves the examination room. To this end a camera or a camera system may be used in combination for example, so that with the help of image processing it may be defined whether a patient and/or operating personnel are entering or leaving the examination room. This may likewise be used in order to be able to define the potential start time more precisely.

In an embodiment, an item of position information of an examination table of the imaging modality may be detected as the fourth item of environmental information in a fourth detection unit. The potential start time is additionally be defined as a function of the fourth item of environmental information.

For example the fourth detection unit may be an element of the detection system of the magnetic resonance system. For example the fourth detection unit or at least parts of the fourth detection unit may be arranged and/or at the examination table or on the patient couch of the imaging modality. Accordingly, it may be detected or defined with the help of the fourth detection unit whether the examination table is located within a patient tunnel of the imaging modality outside of the patient tunnel. Should the examination table be located within the patient tunnel of the imaging modality, then a measurement process or scan process of the patient is due immediately. Should the examination table be located outside of the patient tunnels and thus be in an idle state, it may be deduced that a potential measurement process is not due immediately and that there may still be a little time to elapse until a measurement process.

A further aspect relates to a magnetic resonance system with an imaging modality, that includes a control apparatus, that is configured to control the imaging modality for carrying out a method as previously described.

Through the magnetic resonance system the method previously described may be carried out or executed.

The control apparatus may for example include a control and processing system. The definition of the potential start time and the activation of the at least one component may be carried out or undertaken for example with the help of the control apparatus.

In an embodiment the magnetic resonance system includes at least one detection unit. The at least one detection unit is arranged in an examination room of the magnetic resonance system in which the imaging modality is arranged, and/or is arranged in a control room of the magnetic resonance system. With the help of the at least one detection unit information in the environment of the imaging modality may be detected. For example the at least one detection unit may be used for supervising the imaging modality and for example for supervising a measurement process by the imaging modality.

For example the magnetic resonance system may have a number of detection units, such as the first, second, third and/or fourth detection unit.

The at least one detection unit may for example be arranged or positioned in the examination room in which a measurement process of a patient may be carried out by the imaging modality. In addition or as an alternative the at least one detection unit may be arranged in the control room of the magnetic resonance system or be built into said room. The control room may involve a specific room from where the imaging modality may be controlled, operated and supervised by the operating personnel. Furthermore the control room serves, during a measurement process of the patient, to ensure that no person except for the patient stays in the examination room. During the measurement process on the patient the operating personnel are located in the control room in order to enable them to supervise or check the measurement process on the patient.

In an embodiment the at least one detection unit may be arranged so as to detect a patient and/or an operator in the examination room and/or an operator in the control room. For example the at least one detection unit may be installed in the examination room and/or in the control room or attached in said room to enable it to monitor the examination room in respect of the patient and/or of the operator. In addition or as an alternative the at least one detection unit or an element of the detection unit, such as a movement sensor may be mounted or installed in the control room or in order to be able to detect the operator within the control room.

The detected Information with respect to the patient and/or to the operating personnel may be used in order, with the help of the control apparatus, to be able to establish or predict a start time at which a measurement process will be carried out on the patient. With the aid of the detected information with respect to the patient, the operating personnel and/or the environment of the imaging modality, with the help of the control apparatus corresponding components of the imaging modality may be controlled and for example activated.

Embodiments further provide a computer program that is able to be loaded directly into a memory of the control apparatus of the imaging modality of the magnetic resonance system, with program code for carrying out the method as previously described when the program is executed in the control apparatus of the imaging modality.

Electronically readable data mediums with electronically-readable control information stored thereon may be provided that include at least one computer program as claimed and are configured in such a way that, when the data medium is used in a control apparatus of an imaging modality of a magnetic resonance system, they carry out, at least in part, a method as previously described.

For application cases or application situations that may be produced in the method and that are not explicitly described here, there may be provision, in accordance with the method, for an error message and/or a request for input of a user confirmation to be output and/or for a default setting and/or a predetermined initial state to be set.

DETAILED DESCRIPTION

Figure 1:
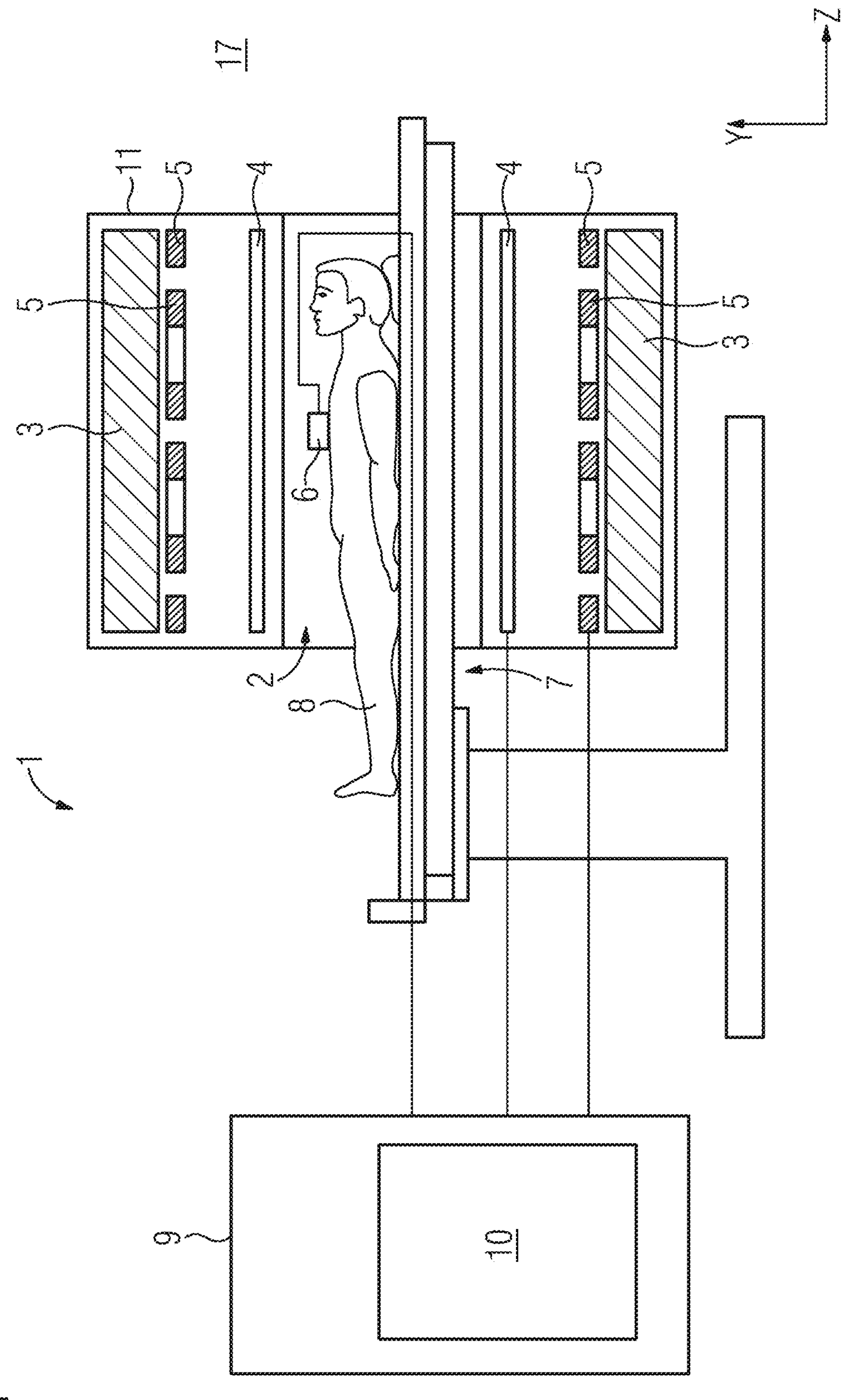
FIG. 1 depicts a schematic view of a magnetic resonance system.

FIG. 1 depicts a schematic diagram of an example of an embodiment of an MRT system 1 (also referred to as a magnetic resonance system).

The MRT system 1 includes a magnet unit with a field magnet 3, that creates a static magnetic field for aligning nuclear spins of an object 8, for example of a patient, in an imaging region. The imaging region is characterized by an extremely homogeneous static magnetic field. The homogeneity relates for example to the magnetic field strength or to its amplitude. The imaging region is located in a patient tunnel 2, that extends in a longitudinal direction Z through the magnet unit. The field magnet 3 may for example be a superconducting magnet, that may create magnetic fields with a magnetic flux density of up to 3 T or more. For lower field strengths however permanent magnets or electromagnets with normally conducting coils may also be used. A patient table or examination table 7 may be movable within the patient tunnel 2.

The magnet unit furthermore includes a gradient coil arrangement 5 with a number of gradient coils, that serve to overlay the static magnetic field gradient fields, i.e. location-dependent magnetic fields, in three spatial directions, for spatial differentiation of the scanned image areas in the imaging region. The gradient coils of the gradient coil arrangement 5 may for example be configured as coils made from normally-conducting wires, that for example may create fields or field gradients orthogonal to one another in the imaging region.

The magnet unit includes a transmit coil arrangement, that for example may include a body coil 4 (also referred to as a whole body coil) as its transmit antenna, that is configured to radiate a radio-frequency signal or excitation signal into the imaging region. The body coil 4 may therefore be understood as an RF transmit coil arrangement of the MRT system 1 or as part of the RF transmit coil arrangement. The body coil 4 may, in an embodiment, also be used to receive resonant MR signals, that are emitted from the object 8. In this case the body coil 4 may also be considered as part of a signal detection apparatus of the MRT system 1. The signal detection apparatus may include a local coil 6, that may be arranged in the immediate vicinity of the object 8, for example on the object 8 or in the patient table 7. the local coil 6 may serve, as an alternative or in addition to the body coil 4, as a receive coil or receive antenna.

The MRT system 1 also includes a control and processing system 9. The control and processing system 9 may include a transceiver unit 10, that is connected to the body coil 4 of the gradient coil arrangement 5 and/or the local coil 6. Depending on the detected MR signals the transceiver unit 10, that may include an ADC ("analog-to-digital converter"), may create corresponding MR data, for example in the k space. The transceiver unit t 10 is also connected to the body coil 4 where necessary and activates said coil for creating RF pulses, such an excitation pulses and/or refocusing pulses. Furthermore the transceiver unit 10 of the control and processing system 9 may also be connected to the gradient coil arrangement 5 and control said arrangement in order to switch slice selection gradients, gradients for frequency and/or phase encoding and/or readout gradients.

For example the MRT system 1 includes an imaging modality 11. The imaging modality 11 may include at least the magnet unit, the patient table 7 and the patient tunnel 2.

Figure 2:
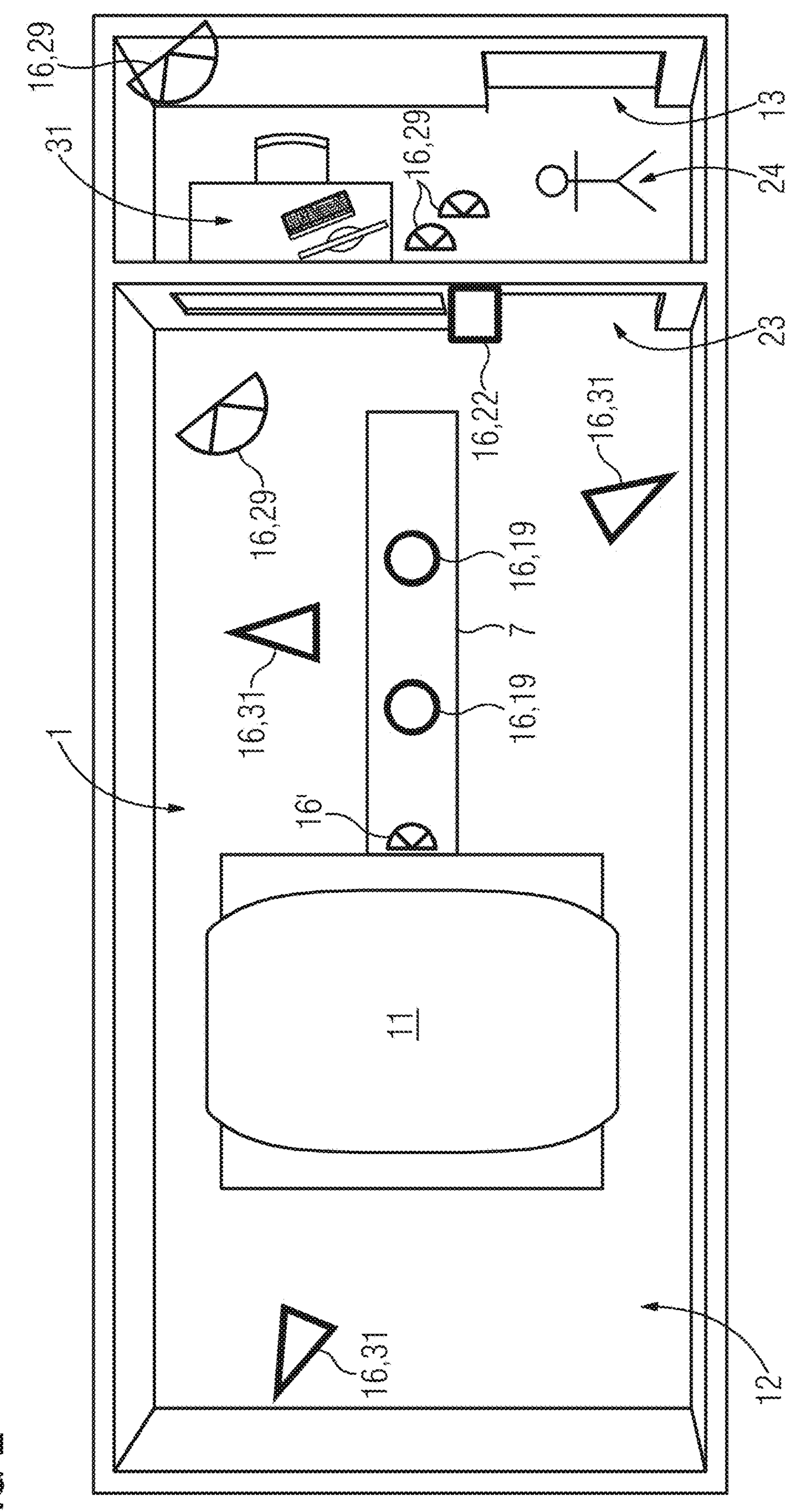
FIG. 2 depicts an embodiment of the magnetic resonance system from FIG. 1 for detection of events and/or items of environmental information of the magnetic resonance system.

FIG. 2 depicts a diagram with an example of the magnetic resonance system 1. Here the magnetic resonance system 1 includes an examination room 12 and a control room 13.

In order to be able to operate the MRT system 1 in a more energy-saving and thus efficient manner, an evaluation of a wide diversity of system states and/or changes of state in respect of the MRT system 1 may be undertaken. This provides at least one component 14 (cf. FIG. 3) and/or a number of components 15 (cf. FIG. 3) of the imaging modality 11 or of the MRT system 1 to be switched on or switched off or made inactive, even if these have relatively long restart times for example, for example in the range of 2 to 600 seconds The at least one component 14 and/or the further component 15 may for example be understood as subsystems of the MRT system 1. Switching off the component 14 may for example be understood as a shutting down, a partial switch-off or a sleep mode. For this there is provision for the at least one component 14 to be activated as a function of a potential start time T (FIG. 4). To this end, by an evaluation and for example an evaluation logic of the control and processing system 9 or of the control apparatus, the potential start time T may be generated. Sensor information is used for this, so that for example events of the magnetic resonance system 1 determined by sensor systems may be determined. For example by the control and processing system 9, that may be referred to for example as the central unit, and event detected by sensors may be processed. On the basis of this event a system state of the MRT system 1 or of the imaging modality 11 may be set. This system state may be transmitted for example by control signal to subcomponents, such as the components 14, 15, so that these subsequently may be put into a corresponding energy-saving mode.

In order to be able to control or activate the components 14, 15 accordingly and to be able to define or determine on the basis of the start time T a measurement process that may be carried out on the patient 8, an environment 17 of the imaging modality 11 or of the magnetic resonance system 1 may be detected or supervised with at least one detection unit 16 or a detection system or a detection facility.

An example of an order for the use of the MRT systems 1 is as follows: Enter examination room 12, Position patient 8 on patient table 7, Move patient table 7 into the patient tunnel 2, and Start the scan or measurement process.

When the patient table 7 is located in a PTAB home position and thus is positioned in a basic state, it may be assumed that no measurement process will be undertaken currently or in the immediate future. Here 10 minutes may be set for example as the possible period of time within which no measurement process or no measurement will be undertaken. Furthermore the control and processing system 9 will recognize from the queue of measurement processes carried out or to be carried out on the system side whether a measurement process is just being or has just been concluded or a new measurement process is being prepared. This information may be used additionally by the control and processing system 9 in order to be used for interpretation of the subsequent events or steps of the MRT system 1 and for example of the start time T.

For example with the help of the at least one detection unit 16 it may be detected or recognized that the patient table 7 is being moved in the direction of the patient tunnel 2. This may be referred to as the event "PTAB start-moving-towards-isocenter". With the aid of this information the respective components 14, 15, that might need as long to be started up as the patient table 7 needs to move from the basic position or its current position to its end position within the patient tunnel 2, may be started up or activated.

For example all components 14, 15, that might need a person of time T1 (cf. FIG. 4) of between 5 and 10 seconds for example.

For components 14, 15 or systems, that need longer than the period of time T1 to start up, it is advantageous to detect further information with respect to the environment 17. For example a position of the patient 8 in relation to the imaging modality 11 may be detected by a first detection unit 19 as at least one detection unit 16. This may for example be taken into account or used as a first item of environmental information 20 (cf. FIG. 3) for the definition of the start time T.

With the help of the first detection unit 19 for example it may be determined whether, and if necessary when, the patient 8 is located on the patient table 7 and is being prepared there for example for the measurement process. The first detection unit 19 may consist for example of a number of individual sensors. Here the detection unit 19 may be configured as a “respiratory sensor” or “pilot tone sensor” or may contain these as elements. For example the detection unit 19 may be arranged in and/or on patient table 7 or integrated into the latter. A further option is for the detection unit 19 to be integrated into the magnet unit, here for example in the “spin coil”.

The detection unit 19 may be used for example to detect or recognize breathing movements of the patient 8. If the unit detects breathing movements then it may be established on the system side that the patient 8 is located on the patient table 7.

For example a change in the RF signals may also be used in order to detect whether or not the patient 8 is located on the patient table 7. As well as the actual state, the switchover for example is easy to recognize since during the switchover large changes in the RF signals, i.e. the breathing frequency, occur. For example “patient on TAB” may be recorded here by sensors as the event. This may in its turn be used for the control of activation of the components 14, 15. If once again be established that the patient 8 is located on the patient table 7, then for example a preparation time of T2 (cf. FIG. 4) of between 10 and 60 seconds may be produced. Accordingly, in this state, the event components 14, 15 may be activated or started up with a maximum start-up time with a duration of T1 plus T2.

Furthermore an opening and/or a closing of a door 23 of the examination room 12 may be detected with a second detection unit 22 as a variant of the at least one detection unit 16.

For example the door 23 serves to enable the patient 8 and/or the operating personnel 24, such as medical technicians, to move about in the examination room 12. For example the door 23 may make it possible to pass from the control room 13 into the examination room 12.

The second detection unit 22 may for example involve a door contact or an electronic door contact sensor.

For example the second detection unit may be configured in such a way that it may be recognized or detected whether the patient 8 and/or an operator 24 is entering or leaving the examination room 12. To this end further camera systems and for example image processing systems may be used to distinguish between the patient 8 and the operating personnel 24. For example it may be determined or detected with the help of the second detection unit 22 that the patient 8 is entering the examination room 12.

For example a period of time T3 (cf. FIG. 4) between the opening of the door 23 and the positioning of the patient 8 on the patient table 7 may amount to between 10 and 30 seconds. Thus “walk to PTAB 25” (cf. FIG. 4) may be detected here as an event by the sensor. Furthermore open door 26 (cf. FIG. 4) may be detected as a possible event here. Here, once again with the help of the first detection unit 19, it may be recognized when the patient 8 has been positioned on the patient table 7. This may in its turn be recognized with the event “put patient on PTAB 27” (cf. FIG. 4). Thus, with the help of the detected second item of environmental information 28 (cf. FIG. 3) the entry of persons into and/or their departure from the examination room 12 may be detected. Here components 14, 15 may thus be started up or activated or controlled that have a start-up time in the range of a period of time T1+T2+T3.

For example additional information from cameras, such as for example a 3D camera, or a patient monitoring camera, may be evaluated with image processing and as an alternative or in addition may be used to be able to detect or establish corresponding events or situations.

Specifically movements of the patient 8 and/or of the operating personnel 24, for example as the third item of environmental information 30 (cf. FIG. 3), may be detected with a third detection unit 29. The third detection unit 29 may be configured for example as a movement alarm or movement sensor, for example be configured as a plurality of movement sensors, as shown by way of example in FIG. 2.

With the help of the third detection unit 29 it may be recognized for example whether the patient 8 and/or the operating personnel 24 are located in the examination room 2. The third detection unit 29 may for example also recognize whether someone leaves or enters the examination room 12 and generate a corresponding event patient entering room from this. This event may be used for example in order on the one hand to determine the start time T and control or start up components 14, 15 accordingly that have a start-up time of greater than T1+T2+T3.

Furthermore, with the help of the detection unit 29, information or movements with respect to the control room 13 may be detected. Here for example a movement sensor may be arranged as a detection unit 29 on a ceiling of the control room 13 or in the area of a control center, from where the operating personnel 24 may supervise a measurement process with the imaging modality 11.

Depending for example on whether the preparations, such as for example registering the patient 8 and starting measurements or sequences, have been recognized before the positioning of the patient on the patient table 7 or thereafter, it will be recognized that there may also be an additional time needed for this to be added before the start of the measurement. For example in the preparation of the measurement process before patient preparation there may be a time to the start of measurement T1+T2+T3+T4 after occurrence of a movement recognition. The preparation of the measurement process after patient preparation may have a duration until start of measurement of T4 after occurrence of a movement event or a movement recognition.

For example the detection unit 29 or the individual sensors of the detection unit 29 may be camera-based with an infrared-based image processing or also movement alarm, ultrasound sensors or radio-frequency sensors.

Figure 3:
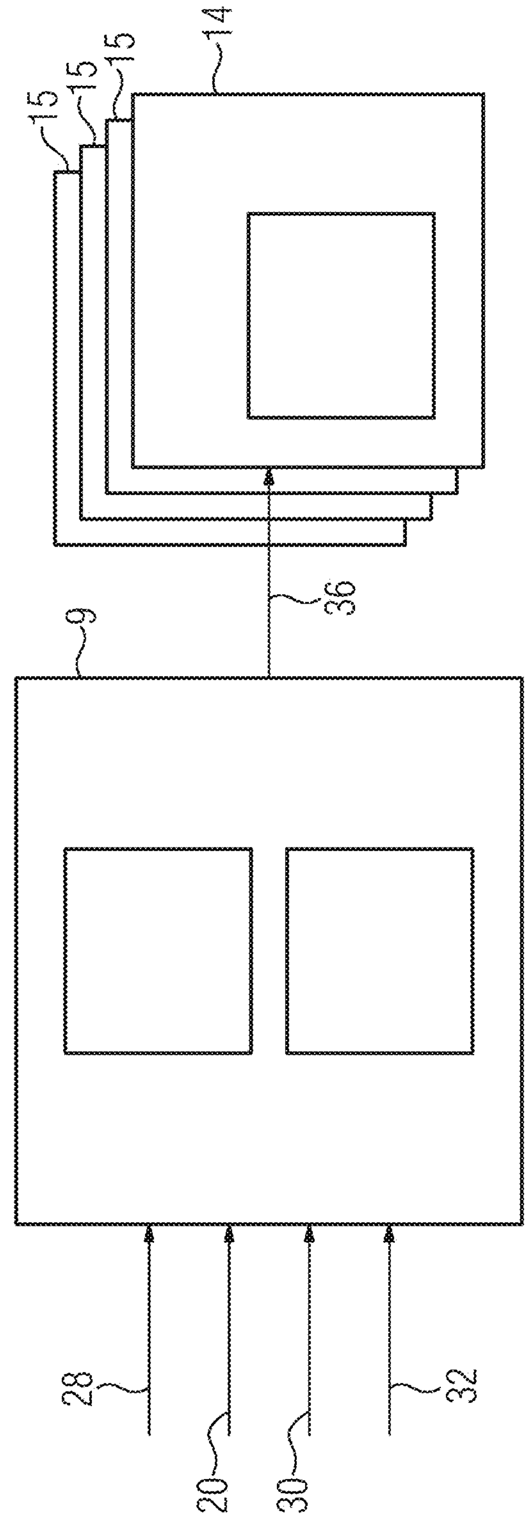
FIG. 3 depicts an embodiment for determination of activation times and/or operating modes of components of the magnetic resonance system from FIG. 1 on the basis of the detected data from FIG. 2.
Figure 4:
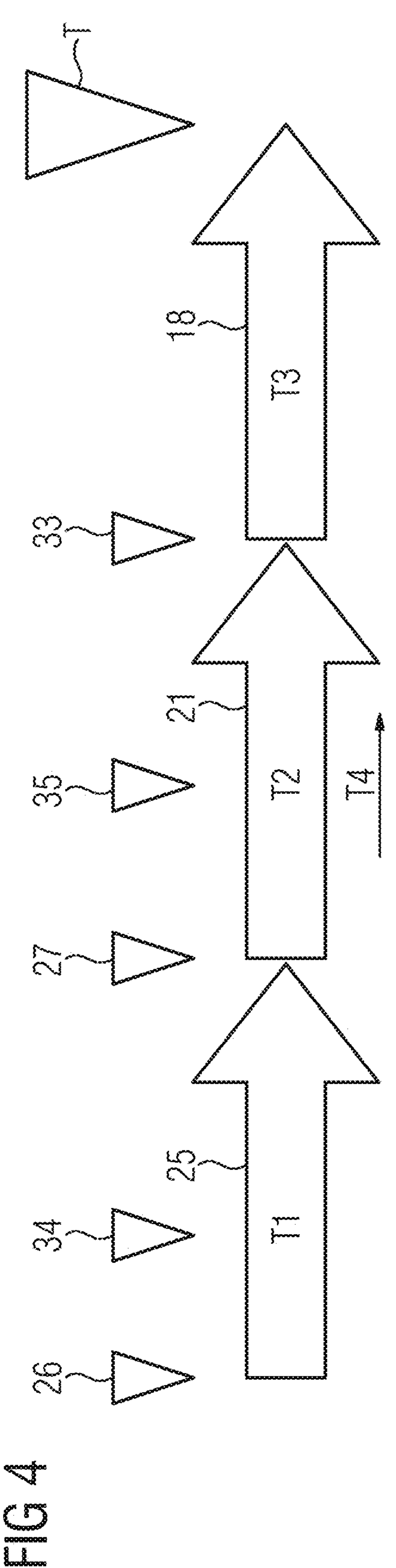
FIG. 4 depicts an example of the timing of the sequence of events before a possible measurement process of the magnetic resonance system from FIG. 1 according to an embodiment.

Furthermore, an item of position information of the patient table 7 or of the examination table may be detected with a fourth detection unit 31 as a fourth item of environmental information 32 (cf. FIG. 3). Cameras or camera systems may be used here for example. For example, with the help of the fourth detection unit 31 the event 18 in which the patient table 7 is already being moved, or an event “move PTAB” 33 (cf. FIG. 4), in which there is an immediately impending movement of the patient 7, may be captured or detected.

Furthermore an event 34 (cf. FIG. 4) may be detected as “detect motion” and likewise be taken into consideration for the activation of the components 14, 15 and the establishing of the start time T with the at least one detection unit 16.

During the event 21 “prepare patient”, as a further item of environmental information to be detected or as a further event to be detected, “Plug local coils” (cf. FIG. 4) may be recognized as an additional event 35. Thus it is detected there as a possible item of environmental information that the patient 8 is still be prepared by the operating personal 24 for the measurement process.

Furthermore additional sensors and/or detection units, that are still to be explained and/or shown, are used. Here for example pilot tone sensors and/or respiratory sensors may be used to detect a presence of the patient 8 on the patient table 7. furthermore weight sensors, pressure sensors and/or proximity sensors may be used to detect the patient 8 on the patient table 7. The sensors may for example be integrated into the patient table 7 or within the imaging modality 11. For example the widest diversity of types of sensor systems may be used for the detection of events or of the item of environmental information.

The detected events and/or the detected items of environmental information 20, 28, 30, 32 may be transferred to or provided to the control and processing system 9 (cf. FIG. 3), and then for example the start time T, at which the imaging system 11 is ready to carry out a measurement process on the patient 8 may be determined. To this end, once again with the help of the control and processing system 9, a corresponding control signal 36 (cf. FIG. 3) is generated and transferred to the components 14, 15, so that for the respective components 14, 15 an activation time and/or an operating mode may be set or adjusted or predetermined.

Thus, with the help of the control and processing system 9, a start time may be calculated for each component 14, 15, at which the respective component 14, 15 is to be started up and should thus be ready.

Likewise, it may be defined with the aid of the control and processing system 9 whether the components 14, 15 are to be put into a "Ready-to-Scan mode", "Sleep mode" and/or "Deep-Sleep mode". Here furthermore through the items of environmental information and/or the events and thus the status of the MRT system 1, a specific order for the starting-up of the components 14, 15 may be determined, so that through this specific order of starting up the components 14, 15 an energy saving may be achieved. Depending on the respective started-up component 14, 15, the item of environmental information and/or the respective event a corresponding acoustic, optical and/or haptic notification or warning may be output to the patient 8 or the operator 24, so that the persons may recognize the respective state of the MRT system 1.

In addition the corresponding information may be used to carry out settings of the smart light. With the help of the smart light as an optical output unit, by a corresponding light or a corresponding light color to be displayed, the respective system states of the MRT systems 1 may be visually displayed.

For example the explanations show how various parameters with respect to the MRT system 1 may be established, in order thereafter to predict or forecast the time until the start of measurement, in order, on the basis of its switched-off components with different lengths of start-up time, to switch said components on again in the right order.

Thus an improvement in the energy consumption of the MRT system 1 may be achieved by detection of patient 8 on the patient table 7 and user movements in the examination room 12.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that the dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for operating an imaging modality of a magnetic resonance system, the method comprising:

detecting at least one item of environmental information in an environment of the imaging modality with at least one detection unit of the magnetic resonance system;

defining a potential start time depending on the at least one detected item of environmental information; and activating, by powering-up, preparing, or preconditioning and before the measurement process begins, at least one component of the imaging modality according to a predefined activation sequence defined based on the potential start time and the detected at least one item of environmental information, the predefined activation sequence specifying an order in which further components of the imaging modality are activated such that each component of the imaging modality is ready at the potential start time.

2. The method of claim 1, wherein the potential start time is defined based on a detection time of a detection of the at least one item of environmental information.

3. The method of claim 2, wherein a point in time is predicted as the potential start time at which a measurement process on a patient may be begun with the imaging modality based on the detection time and the at least one item of environmental information.

4. The method of claim 1, wherein based on the potential start time, the at least one component of the imaging modality is activated in such a way by an activation time of the at least one component and/or an operating mode of the at least one component being defined.

5. The method of claim 1, wherein a respective activation time is defined by the order for each component.

6. The method of claim 1, wherein depending on at least one activated component of the imaging modality an optical, acoustic and/or haptic notification is output to a patient and/or to an operator of the imaging modality.

7. The method of claim 1, wherein the potential start time is additionally determined depending on a past measurement process of the imaging modality.

8. The method of claim 1, wherein a position of a patient in relation to the imaging modality is detected with a first detection unit as a first item of environmental information, wherein the potential start time is additionally defined depending on the first item of environmental information.

9. The method of claim 8, wherein an opening and/or a closing of a door of an examination room in which the imaging modality is arranged is detected as a second item of environmental information with a second detection unit, wherein the potential start time is additionally defined depending on the second item of environmental information.

10. The method of claim 9, wherein movements of a patient and/or of an operator in the environment of the imaging modality are detected with a third detection unit as a third item of environmental information, wherein the potential start time is additionally defined depending on the third item of environmental information.

11. The method of claim 10, wherein an item of position information of a patient table of the imaging modality is detected with a fourth detection unit as a fourth item of environmental information, wherein the potential start time is additionally defined depending on the fourth item of environmental information.

12. A magnetic resonance system comprising:

an imaging modality including a control apparatus that is configured to control the imaging modality for:

detecting at least one item of environmental information in an environment of the imaging modality with at least one detection unit of the magnetic resonance system;

defining a potential start time depending on the at least one detected item of environmental information; and activating, by powering-up, preparing, or preconditioning and before the measurement process begins, at least one component of the imaging modality according to a predefined activation sequence defined based on the potential start time and the detected at least one item of environmental information, the predefined activation sequence specifying an order in which further components of the imaging modality are activated such that each component of the imaging modality is ready at the potential start time.

13. The magnetic resonance system of claim 12, wherein the magnetic resonance system further comprises:

at least one detection unit that is arranged in an examination room of the magnetic resonance system in which the imaging modality is arranged and/or in a control room of the magnetic resonance system.

14. The magnetic resonance system of claim 13, wherein the at least one detection unit is arranged so as to detect a patient and/or an operator in the examination room and/or an operator in the control room.

* * * * *